United States Patent [19]

Adams, Jr. et al.

[11] Patent Number: 5,186,770
[45] Date of Patent: Feb. 16, 1993

[54] BIS(2-NITRO-2-AZAPROPYL) ETHER

[75] Inventors: Theodore C. Adams, Jr., Beltsville; Horst G. Adolph, Silver Spring, both of Md.

[73] Assignee: The United States of America as represented by the Secretary of the Navy, Washington, D.C.

[21] Appl. No.: 626,501

[22] Filed: Jun. 29, 1984

[51] Int. Cl.$^5$ .................. C07C 111/00; C06B 25/34
[52] U.S. Cl. ..................................... 149/92; 564/107; 564/109
[58] Field of Search .................. 564/107, 109; 149/74, 149/92

[56] References Cited

FOREIGN PATENT DOCUMENTS 268402 10/1970 U.S.S.R. .............................. 564/107

OTHER PUBLICATIONS

C.A., vol. 81(5), 24946m (1974).
Korepin, A. G., et al., IZV. AKAD. NAUK SSSR, Ser. Khim, 1974 (2), pp. 474–477.
C.A., vol. 80 (15), 81960q (1974).
Gafurov, R. G., et al., IZV. AKAD. NAUK SSSR, Ser. Khim., 1973 (12), pp. 2825–2826.

*Primary Examiner*—Richard D. Lovering
*Attorney, Agent, or Firm*—Kenneth E. Walden; Roger D. Johnson

[57] ABSTRACT

Bis(2-nitro-2-azapropyl) ether which is prepared by reacting one mole 1-hydroxy-2-nitro-2-azapropane with one mole of 2-nitro-2-azapropyl trifluoroacetate or 2-nitro-2-azapropyl acetate.

9 Claims, 1 Drawing Sheet

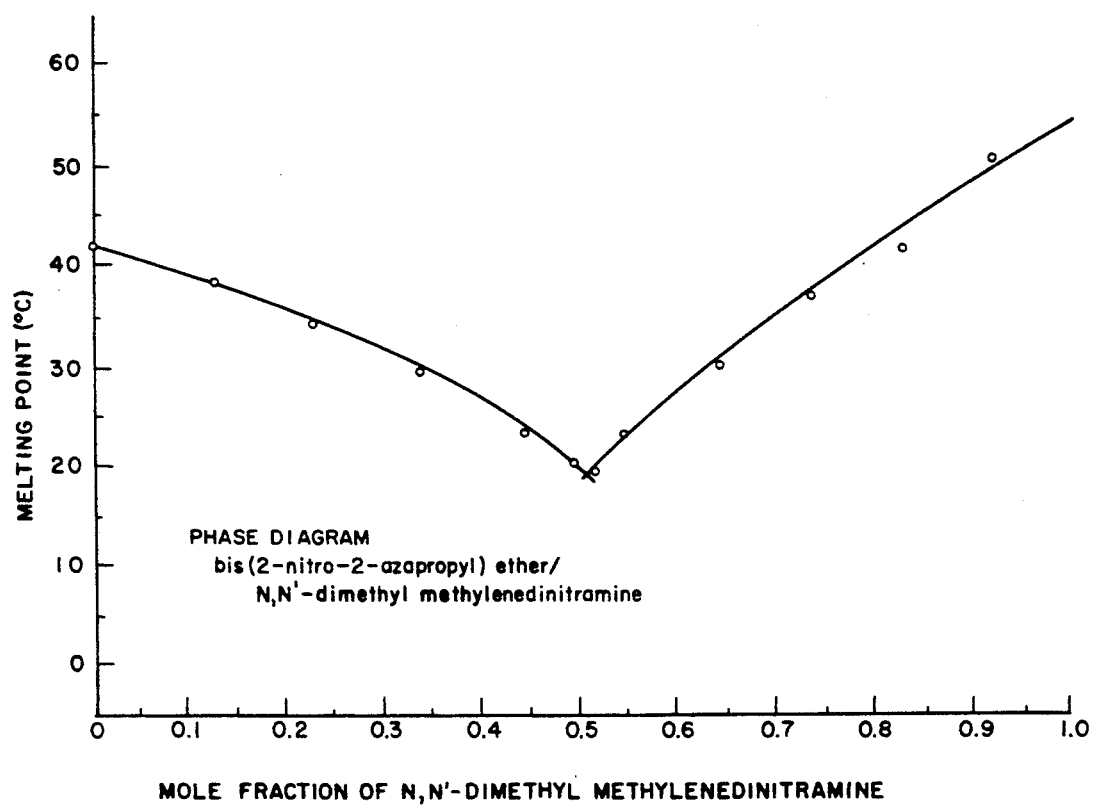

BIS(2-NITRO-2-AZAPROPYL) ETHER

BACKGROUND OF THE INVENTION

This invention relates to ethers and more specifically to ethers containing nitroamine groups.

State-of-the-art high energy plasticizers which have been and are being used in energetic compositions are nitroglycerin (NG) and bis(2,2,2-fluorodinitroethyl) formal (FEFO). While these materials represent the best compromise among available plasticizers, they have many undesirable properties such as high volatility, high melting point, modest plasticizing ability, high toxicity, high sensitivity, and, in part, low thermal stability and high cost.

In addition, it would be desirable to provide plasticizers which will contribute to lower flame temperatures for propellants.

SUMMARY OF THE INVENTION

Accordingly, an object of this invention is to provide a new energetic compound.

Another object of this invention is to provide a new energetic compound for use in propellant plasticizers.

A further object of this invention is to provide a new energetic compound which will contribute to lower flame temperatures in propellants.

These and other objects of this invention are achieved by providing, bis(2-nitro-2-azapropyl) ether which is prepared by reacting one mole of an acetate of the formula

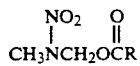

wherein R is —CF$_3$ or —CH$_3$, with one mole of 1-hydroxy-2-nitro-2-azapropane.

BRIEF DESCRIPTION OF THE DRAWING

The FIGURE presents the melting points for binary mixtures of bis(2-nitro-2-azapropyl) ether and N,N'-dimethyl methylenedinitramine.

DETAILED DESCRIPTION OF THE PREFERRED EMBODIMENT

Plasticizers containing only nitramine moieties as energetic groups are desirable for certain propellant applications because they contribute to low flame temperatures. However, because of the tendency of nitramines to have high melting points, no suitable nitramine plasticizers are currently in use or available.

Bis(2-nitro-2-azapropyl) ether,

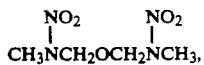

is a relatively low melting nitramine (m.p. 41°–42° C.) with potential plasticizer properties for polymers such as cellulose acetate butyrate (CAB), nitrocellulose (NC), and acrylate elastomers. This can be concluded from the demonstrated plasticizing ability for nitrocellulose of the higher melting N,N'-dimethyl methylenedinitramine (DMMD),

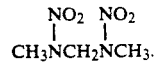

Bis(2-nitro-2-azapropyl) ether, like N,N'-dimethyl methylenedinitramine, is by itself too high melting to be useful as a unitary plasticizer; but when mixed with suitable additives, a melting point sufficiently low can result. See the FIGURE which presents a graph showing the melting point versus composition for various binary mixtures of bis(2-nitro-2-azapropyl) ether and N,N'-dimethyl methylenedinitramine. Preferably the binary mixture comprises from 30 to 70 molar percent of bis(2-nitro-2-azapropyl) ether with the remainder being N,N'-dimethyl methylenedinitramine; more preferred is a 1:1 molar eutectic mixture which has the minimum melting point of 19°–20° C. The 1:1 molar eutectic mixture readily plasticizes nitrocellulose (NC) and cellulose acetate butyrate (CAB). This 1:1 eutectic mixture was also found to have better compatibility than nitrate ester or C-Nitro compounds with unsaturated materials such as cyclohexene, and thus may be a suitable plasticizer for the widely used polybutadiene binders. Finally, the 1:1 molar eutectic mixture of bis(2-nitro-2-azapropyl) ether and N,N'-dimethyl methylenediamine has a good energy content and excellent thermal stability.

Bis(2-nitro-2-azapropyl) ether can be prepared by reacting one mole of 1-hydroxy-2-nitro-2-azapropane with one mole of 2-nitro-2-azapropyl acetate in the presence of a Lewis acid catalyst. The preferred Lewis acid catalyst is boron trifluoride. The preferred solvent is dichloromethane, but other inert halocarbon solvents also can be used.

A preferred method of preparing bis(2-nitro-2-azapropyl) ether is to react one mole of 1-hydroxy-2-nitro-2-azapropane with one mole of 2-nitro-2-azapropyl trifluoroacetate. The reaction is run in a polar solvent, preferably acetonitrile. No catalyst is needed. This reaction is run at a temperature of from −30° C. to +50° C. and preferably from −25° C. to +25° C., under a vacuum which removes the trifluoroacetic acid generated by the reaction. Example 3 illustrates this reaction.

The 2-nitro-2-azapropyl trifluoroacetate is prepared by reacting one mole of trifluoroacetic anhydride with one mole of 1-hydroxy-2-nitro-2-azapropane. The preferred reaction temperature is from about −5° C. to about 0° C. A suitable halocarbon solvent such as dichloromethane is used as the solvent. Example 2 illustrates this reaction.

The general nature of the invention having been set forth, the following examples are presented as specific illustrations thereof. It will be understood that the invention is not limited to these specific examples but is susceptible to various modifications that will be recognized by one of ordinary skill in the art.

The starting material 2-nitro-2-aza-1-propanol was prepared by the following method quoted from G. A. Gareev et al, *Zhur Org. Khim* (*Engl. Transl.*) 7, 1971, p. 631

"To 52.5 ml of 32% formaldehyde we added 30.4 g of methylnitroamine. The mixture was stirred for one hour at 20° C., and the product was extracted with methylene chloride (3×50 ml). The extract was dried with magnesium sulfate and evaporated under vacuum. The colorless liquid which remained was . . . [2-nitro-2-aza-1-propanol]. The yield was 41.6 g (98%), d$_4^{20}$ 1.3083, $n_D^{20}$ 1.4720, $MR_D$ 22.69 (calculated 22.42). IR spectrum, cm$^{-1}$: 1535 and 1550 (NNO$_2$), 3545 (OH). The liquid crystallized on standing in the cold. The crystals melted at 33°–34° C. Found %: C 22.80, H 6.10, N 26.50. C$_2$H$_6$N$_2$O$_3$. Calculated %: C 22.64, H 5.66, N 26.42."

EXAMPLE 1

2-nitro-2-azapropyl acetate (Prior Art Method)

To a stirred mixture of 10.6 g of 2-nitro-2-aza-1-propanol and 25 ml of dichloromethane under a nitrogen atmosphere was added dropwise and with ice-cooling 12 g of acetyl chloride. The cooling bath was removed and the mixture was slowly heated to reflux. After 3 hours the solution was allowed to cool and was then triturated with 50 ml of ice water. The organic phase was separated, dried (MgSO$_4$), and distilled. The product 2-nitro-2-azapropyl acetate had b.p. 56°–57° C. at 0.07 mm Hg.

EXAMPLE 2

2-nitro-2-azapropyl trifluoroacetate

Trifluoroacetic anhydride (80 ml, 118.4 g, 0.56 moles) was added to a stirred solution of 1-hydroxy-2-nitro-2-azapropane (40.0 g, 0.38 moles) in dichloromethane (60 ml) at −5° to 0° C. during 1½ hours. The resulting solution was then distilled without warming at 20 mm, then to 3 mm. The product was distilled at 1.5 mm, 65° C., to give 2-nitro-2-azapropyl trifluoroacetate; yield: 48 g (63%).

'H-N.M.R. (CDCl$_3$/TMS$_{int}$):δ=3.58 (s, 3 H), 6.08 ppm (s, 2 H).

EXAMPLE 3 bis(2-nitro-2-azapropyl) ether

1-Hydroxy-2-nitro-2-azapropane (0.52 g, 4.9 mmol) and acetonitrile (0.5 ml) were stirred under nitrogen at −20° C. as 2-nitro-2-azapropyl trifluoroacetate (1.09 g, 5.4 mmol) was added in one portion. The reaction flask was immediately connected to a vacuum pump and brought to 1–2 mm during several minutes. The reaction temperature was allowed to warm to ambient during 2½ hours, a precipitate forming at about 10° C. After stirring an additional 1½ hours, the vacuum was removed and cold ether (5 ml) was stirred with the solid mass 5 minutes before filtering bis(2-nitro-2-azapropyl) ether; yield: 0.83 g (87%); m.p. 30°–38.5° C. Recrystallization from ether gave bis(2-nitro-2-azapropyl) ether; yield: 0.55 g (58%); m.p. 38°–41° C. The analytical sample melted at 40.6°–42° C.

'H-N.M.R. (CDCl$_3$/TMS$_{int}$):δ=3.47 (s, 6 H); 5.38 ppm (s, 4 H).

Obviously, numerous modifications and variations of the present invention are possible in light of the above teachings. It is therefore to be understood that within the scope of the appended claims the invention may be practiced otherwise than as specifically described herein.

What is claimed and desired to be secured by Letters Patent of the United States is:

1. bis(2-nitro-2-azapropyl) ether.

2. An energetic plasticizer consisting essentially of a binary mixture of from about 30 to about 70 mole percent of bis(2-nitro-2-azapropyl) ether with the remainder being essentially N,N'-dimethyl methylenedinitramine.

3. The plasticizer of claim 2 which is a 1:1 molar eutectic mixture of bis(2-nitro-2-azapropyl) ether and N,N'dimethyl methylenedinitramine.

4. A method of preparing bis(2-nitro-2-azapropyl) ether comprising:
   (1) reacting one mole of 2-nitro-2-azapropyl trifluoroacetate with one mole of 1-hydroxy-2-nitro-2-azapropane in a polar solvent at a temperature from −30° C. to +50° C. to form bis(2-nitro-2-azapropyl) ether; and
   (2) isolating the product bis(2-nitro-2-azapropyl) ether.

5. The method of claim 4 wherein step (1) is run at a temperature of from −25° C. to +25° C.

6. The method of claim 4 wherein step (1) is performed under vacuum to remove the trifluoroacetic acid generated by the reaction.

7. The method of claim 4 wherein the reaction of step (1) is run in acetonitrile.

8. A method of preparing bis(2-nitro-2-azapropyl) ether comprising:
   (1) reacting one mole of 2-nitro-2-azapropyl acetate with one mole of 1-hydroxy-2-nitro-2-azapropane in the presence of a Lewis acid catalyst in an inert halocarbon solvent to form bis(2-nitro-2-azapropyl) ether; and
   (2) isolating the product bis(2-nitro-2-azapropyl) ether.

9. The method of claim 8 wherein the Lewis acid is boron trifluoride.

* * * * *